United States Patent

Begley et al.

Patent Number: 5,912,110
Date of Patent: *Jun. 15, 1999

[54] PHOTOGRAPHIC COUPLER CAPABLE OF RELEASING A PHOTOGRAPHICALLY USEFUL GROUP

[75] Inventors: William James Begley, Webster; Teh Hsuan Chen; Frank Dino Coms, both of Fairport; Donald Singleton, Jr., Rochester, all of N.Y.

[73] Assignee: Eastman Kodak Company, Rochester, N.Y.

[*] Notice: This patent is subject to a terminal disclaimer.

[21] Appl. No.: 08/872,496

[22] Filed: Jun. 10, 1997

Related U.S. Application Data

[62] Division of application No. 08/590,644, Jan. 24, 1996, Pat. No. 5,670,301
[60] Provisional application No. 60/000,766, Jun. 30, 1995.

[51] Int. Cl.$^6$ .............................. G03C 1/08; G03C 7/26; G03C 7/32
[52] U.S. Cl. .......................... 430/544; 430/543; 430/955; 430/956; 430/957; 430/958; 430/959; 430/960
[58] Field of Search ................................ 430/543, 544, 430/955, 956, 957, 958, 959, 960

[56] References Cited

U.S. PATENT DOCUMENTS

| | | | |
|---|---|---|---|
| 4,248,962 | 2/1981 | Lau | 430/382 |
| 4,409,323 | 10/1983 | Sato et al. | 430/957 |
| 4,861,701 | 8/1989 | Burns et al. | 430/955 |
| 5,670,301 | 9/1997 | Begley et al. | 430/544 |
| 5,686,234 | 11/1997 | Begley et al. | 430/544 |

FOREIGN PATENT DOCUMENTS

| | | |
|---|---|---|
| 0 464 612 | 1/1992 | European Pat. Off. . |
| 0 499 279 | 2/1992 | European Pat. Off. . |
| 0 529 436 | 3/1993 | European Pat. Off. . |
| 0 540 118 | 5/1993 | European Pat. Off. . |
| 0 576 088 | 12/1993 | European Pat. Off. . |
| 0 438 129 | 4/1995 | European Pat. Off. . |
| 62-217242 | 9/1987 | Japan . |

*Primary Examiner*—Geraldine Letscher
*Attorney, Agent, or Firm*—Sarah Meeks Roberts

[57] ABSTRACT

A photographic element comprising a support having situated thereon at least one silver halide emulsion layer, the layer containing a photographic coupler represented by the formula $$\text{COUP} - \text{T}^1 - \text{HETERO} - \underset{\underset{R^2}{|}}{\overset{\overset{R^1}{|}}{C}} - \text{PUG}$$

wherein

COUP is a coupler moiety having a coupling site to which $T^1$ is attached;

$T^1$ is a timing or linking group which releases from COUP during processing and which functions by electron transfer down a conjugated chain, or by nucleophilic displacement reaction, to release from HETERO;

HETERO is a heterocyclic group containing at least two heteroatoms independently selected from oxygen, nitrogen, or sulfur, wherein one of the heteroatoms is directly attached to $T^1$;

$R^1$ and $R^2$ are independently selected from hydrogen, or an aliphatic, carbocyclic, or heterocyclic group, or may be bonded together to form a 5, 6, or 7 membered ring; and PUG is a photographically useful group.

2 Claims, No Drawings

PHOTOGRAPHIC COUPLER CAPABLE OF RELEASING A PHOTOGRAPHICALLY USEFUL GROUP

CROSS REFERENCE TO RELATED APPLICATION

This is a divisional of application Ser. No. 08/590,644, filed Jan. 24, 1996, now U.S. Pat. No. 5,670,301, for which reference is made to an priority claimed from U.S. provisional application Ser. No. 60/000,766, filed Jun. 30, 1995, entitled PHOTOGRAPHIC ELEMENT CONTAINING A COUPLER CAPABLE OF RELEASING A PHOTOGRAPHICALLY USEFUL GROUP.

FIELD OF THE INVENTION

This invention relates to photographic elements, processes and couplers, the couplers being of the type that release a photographically useful group (PUG) through a timing or linking group upon reaction with oxidized color developing agent during processing.

BACKGROUND OF THE INVENTION

Various ways are recognized in the photographic industry for releasing a PUG from a compound, such as a coupler, in a photographic material and process. Release can be direct, for example upon reaction of the coupler with oxidized color developing agent during processing, or it can be indirect through a linking or timing group. Linking and timing groups provide the ability to control the timing and rate of release of a PUG in a photographic element, as well as the rate and distance of diffusion of the PUG in the element during processing.

U.S. Pat. No. 4,248,962 describes compounds that release a PUG, such as a development inhibitor group, through a timing group which functions by (intramolecular) nucleophilic displacement reaction. Other examples of compounds that are capable of releasing a PUG are described in U.S. Pat. Nos. 4,409,323 and 4,861,701. In U.S. Pat. No. 4,409,323, compounds are described which release a PUG by a mechanism which involves electron transfer down a conjugated chain. In U.S. Pat. No. 4,861,701, sequences of timing groups are utilized to release a PUG and to provide desirable control over the impact of the PUG on photographic properties.

European Patent Applications 0 499 279 and 0 438 129 describe photographic couplers and compounds which allegedly provide superior release rates over compounds described in the aforementioned U.S. Pat. No. 4,861,701. Specifically, these applications describe photographic compounds having a heterocyclic timing nucleus (typically pyrazole) attached to a coupler moiety through an —O—C(O)— or —OCH$_2$— group, or other group capable of releasing the heterocyclic timing nucleus by electron transfer down an unconjugated chain. However, these compounds, especially those described in European Patent Application 0 499 279, do not provide for any flexibility in their rate of release of a PUG, or in their synthetic design, as they are limited by the presence of the particular first timing or linking group. More importantly, though, the compounds in both of these applications exhibit poor stability and decompose when stored for prolonged periods under tropical conditions. Thus, they are of limited practical value in today's photographic industry.

A need has therefore existed for a photographic coupler that is synthetically simple to manufacture; that is capable of providing a wide range of release rates depending upon the particular selection of timing or linking groups and the substituents thereon; and that is stable when stored for prolonged periods, especially under tropical conditions. The coupler which is needed should be capable of releasing a PUG, such as a development inhibitor, thereby providing interlayer interimage effects and increased acutance for the image produced upon processing photographic material containing the coupler.

SUMMARY OF THE INVENTION

The present invention provides a photographic coupler as described below, and a photographic element comprising a support having situated thereon at least one silver halide emulsion layer, the layer containing a photographic coupler represented by the formula

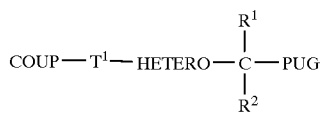

wherein
COUP is a coupler moiety having a coupling site to which $T^1$ is attached;
$T^1$ is a timing or linking group which releases from COUP during processing and which functions by electron transfer down a conjugated chain, or by nucleophilic displacement reaction, to release from HETERO;
HETERO is a heterocyclic group containing at least two heteroatoms independently selected from oxygen, nitrogen, or sulfur, wherein one of the heteroatoms is directly attached to $T^1$;
$R^1$ and $R^2$ are independently selected from hydrogen, or an aliphatic, carbocyclic, or heterocyclic group, or may be bonded together to form a 5, 6, or 7 membered ring; and
PUG is a photographically useful group.

Also provided in accordance with the present invention is a process of forming an image in an exposed photographic silver halide element containing a coupler as described above comprising developing the element with a color photographic silver halide developing agent.

The invention provides the opportunity to achieve improved image modification through the use of new type of coupler capable of releasing a PUG upon photographic processing. The new coupler is synthetically simple to manufacture; provides improved release rates over couplers known in the art; and is much more stable than previously known PUG releasing couplers containing a heterocyclic timing or linking group. The coupler utilized in the invention, particularly when PUG is a development inhibitor, provides improved interlayer interimage effects and acutance levels in photographic elements in which it is contained.

DETAILED DESCRIPTION OF THE INVENTION

In the photographic coupler utilized in accordance with the present invention, the coupler moiety, as represented by COUP, can be any moiety that will react with oxidized color developing agent during processing to cleave the bond between $T^1$ and the coupler moiety. The coupler moiety as described herein includes conventional coupler moieties employed to yield both colorless and colored products upon reaction with oxidized color developing agents. Both types of coupler moieties are well known to those skilled in the photographic art and are exemplified in, for example, *Research Disclosure*, September 1994, Item 36544, all published by Kenneth Mason Publications, Ltd., Dudley Annex, 12a North Street, Emsworth, Hampshire PO10 7DQ, ENGLAND.

The coupler moiety can be ballasted or unballasted, and if unballasted, the dye formed upon oxidative coupling is capable of diffusing throughout, or being washed out of, the photographic element. The coupler can be monomeric, or it can be part of a dimeric, oligomeric or polymeric coupler, in which case more than one PUG can be contained in the coupler. The coupler can also form part of a bis compound in which the PUG forms part of a link between two coupler moieties.

Representative coupler moieties suitable for use in the invention are as follows:

COUP

A. Couplers which form cyan dye upon reaction with oxidized color developing agent are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturubersicht," published in Agfa Mitteilungen, Band III, pp. 156–175 (1961), all of which are incorporated herein by reference.

Preferably such cyan dye-forming couplers are phenols and naphthols.

B. Couplers which form magenta dye upon reaction with oxidized color developing agent are described in such representative patents and publications as: U.S. Pat. Nos. 2,600,788; 2,369,489; 2,343,703; 2,311,082; 3,152,896; 3,519,429; 3,062,653; 2,908,573 and "Farbkuppler-eine Literaturubersicht," published in Agfa Mitteilungen,Band III, pp. 126–156 (1961), all of which are incorporated herein by reference.

Preferably such magenta dye-forming couplers are pyrazolones or pyrazolotriazoles.

C. Couplers which form yellow dye upon reaction with oxidized color developing agent are described in such representative patents and publications as: U.S. Pat. Nos. 2,875,057; 2,407,210; 3,265,506; 2,298,443; 3,048,194; 3,447,928 and "Farbkuppler-eine Literaturubersicht," published in Agfa Mitteilungen, Band III, pp. 112–126 (1961), all of which are incorporated herein by reference.

Preferably such yellow dye-forming couplers are acylacetamides, such as benzoylacetamides and pivaloylacetamides.

D. Couplers which form a colorless product upon reaction with oxidized color developing agent are described in such representative patents as: U.K. Patent No. 861,138; and U.S. Pat. Nos. 3,632,345; 3,928,041; 3,958,993 and 3,961,959, all of which are incorporated herein by reference.

Specific representative examples of coupler moieties suitable for use in the invention are as follows:

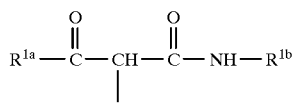

Formula (1A)

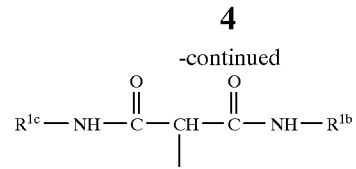

Formula (1B)

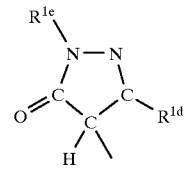

Formula (1C)

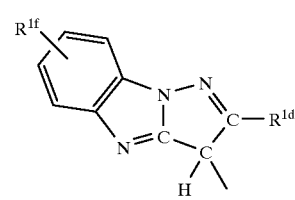

Formula (1D)

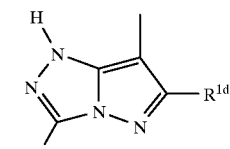

Formula (1E)

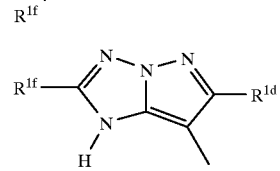

Formula (1F)

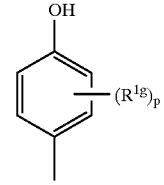

Formula (1G)

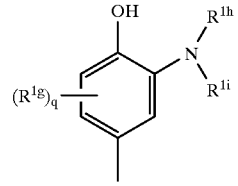

Formula (1H)

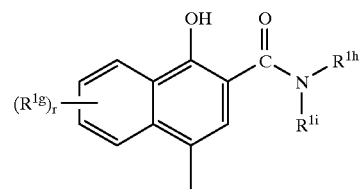

Formula (1I)

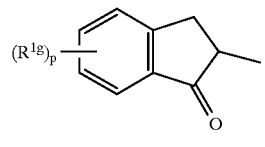

Formula (1J)

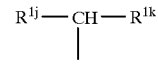

Formula (1K)

The free bond in each of the coupler moieties described above represents the coupling site, which is the position to which the coupling-off group is linked.

In the above formulae, $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, or $R^{1k}$ may contain one or more solubilizing groups which will enable the coupler, upon reaction with oxidized color developing agent, to washout of the photographic element. Such groups, and couplers containing them, are exemplified in U.S. Pat. Nos. 4,482,629; 5,026,628; 5,151,343; 5,250,398; and 5,250,399, which are incorporated herein by reference. Specifically preferred solubilizing groups are selected from a carboxyl, sulfo, carbonamido or hydroxyl group, or salt thereof. It is preferred that when a solubilizing group is present, the coupler is also unballasted so that complete washing out of the coupler can occur. By unballasted, it is meant that each $R^{1a}$ to $R^{1k}$ contain no more than 20 carbon atoms, preferably no more than 12 carbon atoms, and optimally no more than 8 carbon atoms.

$R^{1a}$ to $R^{1k}$, p, q and r in formulae (1A) to (1K) are set forth in more detail as follows. Each of $R^{1a}$ to $R^{1k}$ is independently selected from the group consisting of a substituted or unsubstituted aliphatic, carbocyclic or heterocyclic group. Aliphatic, carbocyclic, and heterocyclic groups as used herein and elsewhere in this application are defined in accordance with the definitions set forth in Grant and Hackh's Chemical Dictionary, fifth ed., McGraw-Hill 1987, and are in accordance with general rules of chemical nomenclature.

Exemplary aliphatic groups include alkyl, alkene, and alkyne groups, specifically methyl, ethyl, propyl, butyl, pentyl, hexyl, octyl, nonyl, decyl, dodecyl, hexadecyl, octadecyl, isopropyl, t-butyl, butenyl, pentenyl, hexenyl, octenyl, dodecenyl, propynyl, butynyl, pentynyl, hexynyl, and octynyl.

Exemplary carbocyclic groups (which include aryl groups) are phenyl, tolyl, naphthyl, cyclohexyl, cyclopentyl, cyclohexenyl, cycloheptatrienyl, cyclooctatrienyl, cyclononatrienyl, cyclopentenyl, anilinyl, and anisidinyl.

Exemplary heterocyclic groups (which include heteroaryl groups) are pyrrolyl, furanyl, tetrahydrofuranyl, pyridinyl, picolinyl, piperidinyl, morpholinyl, thiadiazolyl, thiatriazolyl, benzothiazolyl, benzoxazolyl, benzimidizolyl, benzoselenozolyl, benzotriazolyl, indazolyl, quinolinyl, quinaldinyl, pyrrolidinyl, thiophenyl, oxazolyl, thiazolyl, imidazolyl, selenazolyl, tellurazolyl, triazolyl, tetrazolyl, and oxadiazolyl.

Groups suitable for substitution on each of the above include alkyl groups (for example, methyl, ethyl, hexyl), fluoroalkyl groups (for example, trifluoromethyl), alkoxy groups (for example, methoxy, ethoxy, octyloxy), aryl groups (for example, phenyl, naphthyl, tolyl), hydroxy groups, halogen groups, aryloxy groups (for example, phenoxy), alkylthio groups (for example, methylthio, butylthio), arylthio groups (for example, phenylthio), acyl groups (for example, acetyl, propionyl, butyryl, valeryl), sulfonyl groups (for example, methylsulfonyl, phenylsulfonyl), acylamino groups, sulfonylamino groups, acyloxy groups (for example, acetoxy, benzoxy), carboxy groups, cyano groups, sulfo groups, and amino groups.

p in the above formulae can be an integer of 1 to 4; q can be an integer of 1 to 3; and r can be an integer of 1 to 5.

Preferred coupler moieties suitable for the couplers utilized in the invention are represented by

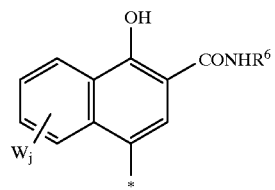

wherein

* designates the coupling site to which $T^1$ is attached;

$R^6$ is selected from hydrogen, or an aliphatic, carbocyclic, or heterocyclic group; and preferably from hydrogen, an alkyl group containing 1–5 carbon atoms, an aryl group containing 6–10 carbon atoms or a heterocyclic group containing 4–8 carbon atoms;

W is selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio, group; and preferably from an alkyl containing 1–5 carbon atoms or a carbamoyl, sulfamoyl, carbonamido, sulfonamido, sulfo, nitro, hydroxyl, carboxyl, amino, alkoxy or alkoxycarbonyl group; and j is 0, 1, 2, 3, or 4, preferably 0 or 1.

Also preferred are coupler moieties represented by

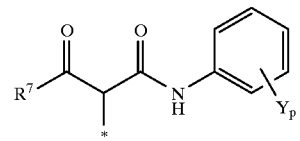

wherein

* designates the coupling site to which $T^1$ is attached;

$R^7$ is selected from an aliphatic, carbocyclic, or heterocyclic group; and preferably from an alkyl group containing 1–10 carbon atoms, an aryl group containing 6–10 carbon atoms or a heterocyclic group containing 4–8 carbon atoms;

Y is selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy or arylthio group; and preferably from an alkyl containing 1–5 carbon atoms, carbamoyl, sulfamoyl, carbonamido, sulfonamido, sulfo, nitro, hydroxyl, carboxyl, amino, alkoxy or alkoxycarbonyl group; and p is 0, 1, 2, 3, or 4, preferably 1 or 2.

The photographic coupler utilized in the invention reacts (i.e. couples) with the oxidized product of a color developing agent to release $T^1$, which is a timing or linking group that functions by nucleophilic displacement reaction (of the type described in, for example, U.S. Pat. No. 4,248,962), or electron transfer down a conjugated chain (of the type described in, for example, U.S. Pat. No. 4,861,701) to release the remainder of the coupler (HETERO—C($R^1$)($R^2$)-PUG). Representative $T^1$ groups are as follows:

Timing or Linking groups, ($T^1$)

1. Acyclic $T^1$ groups capable of nucleophilic displacement reaction:

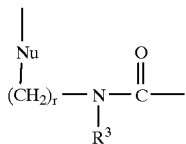

where r is 0 to 5; preferably 2, 3 or 4; Nu is a nucleophilic group, typically

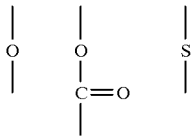

and $R^3$ is hydrogen, or an aliphatic, carbocyclic, or heterocyclic group. Preferably, it is an alkyl of 1 to 20 carbon atoms or aryl of 6 to 20 carbon atoms. More preferably, it is an alkyl of 1 to 4 carbon atoms or an aryl of 6 to 10 carbon atoms.

2. Aromatic $T^1$ groups capable of nucleophilic displacement reaction:

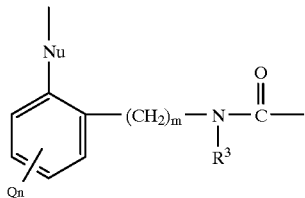

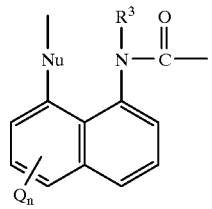

where m is 0, 1, 2 or 3, preferably 0 or 1; and Nu is a nucleophilic group, typically selected from

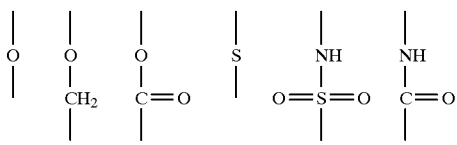

$R^3$ is as defined above; Q is independently selected from the group consisting of an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group. Preferably, Q is an alkyl of 1 to 4 carbon atoms, or a nitro, sulfo, carbonamido or sulfonamido group. n is an integer selected from 0, 1, 2 or 3, and is preferably 0 or 1.

3. Heterocyclic $T^1$ groups capable of nucleophilic displacement reaction:

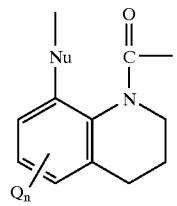

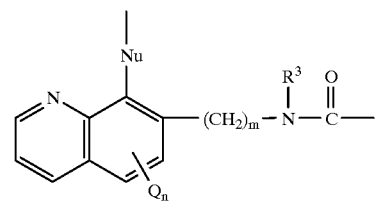

where m, n, Q, Nu and $R^3$ are as defined above.

4. Aromatic $T^1$ groups capable of electron transfer down a conjugated chain.

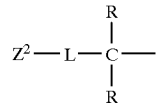

where $Z^2$ is O or an unsubstituted or lower alkyl ($C_{1-C5}$) substituted nitrogen; L is pyridylene, 1,2- or 1,4-phenylene or naphthalene group; and R is independently a hydrogen, alkyl or aryl group.

Other representative timing and linking groups useful as $T^1$ in the present invention are described in U.S. Pat. Nos. 4,421,845; 4,409,323; 4,861,701; 4,886,736; 4,857,447; 4,891,304; and 5,190,846, all of which are incorporated herein by reference.

In the preferred embodiments of the invention, $T^1$ is a group which functions by nucleophilic displacement reaction. As used herein, "nucleophilic displacement reaction" means a reaction in which a nucleophilic center of a compound reacts directly, or indirectly through an intervening molecule, at another site on the compound, that is an electrophilic center, to effect displacement of a group or atom attached to the electrophilic center. Such compounds have a nucleophilic group and electrophilic group spacially related by the configuration of the molecule to promote reactive proximity. The electrophilic group and the nucleophilic group are located in the coupling-off group as described so that a cyclic organic ring, or a transient cyclic organic ring can be easily formed by an intramolecular reaction involving the nucleophilic center and the electrophilic center.

A nucleophilic group is understood to be a grouping of atoms, one of which is electron rich. This atom is referred to as the nucleophilic center, representative examples of which include oxygen, sulfur and nitrogen atoms. An electrophilic group is understood to be a grouping of atoms, one or more of which is electron deficient. This atom(s) is referred to as the electrophilic center, representative examples of which include carbonyl, thiocarbonyl, phosphinyl, and thiophosphinyl. Additional examples of nucleophilic groups, electrophilic groups and linking groups (to be discussed below) can be found in U.S. Pat. No. 4,248,962.

$T^1$ in the preferred embodiments of the invention thus comprises a nucleophilic group (Nu)—which is attached to the coupling site of COUP and which is displaced therefrom upon reaction of COUP with oxidized color developing agent during processing—and an electrophilic group (E)—which is attached to HETERO and which is displaced therefrom by Nu after Nu is displaced from COUP.

The nucleophilic and electrophilic groups are separated from each other by a linking group(X). The linking group spatially relates the nucleophilic group from the electrophilic group so that upon displacement of the nucleophilic group from the coupler moiety, $T^1$ undergoes a nucleophilic displacement reaction with the formation of, preferably, a three to eight membered ring and the cleavage of the bond between the electrophilic group and the heterocyclic group.

The preferred couplers utilized in the invention are thus represented by the formula:

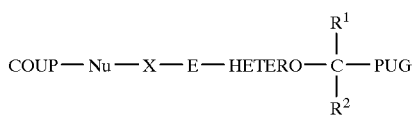

wherein COUP, HETERO, Nu, X, E, and PUG are as defined above. $R^1$ and $R^2$ are also defined above and are independently selected from hydrogen, or an aliphatic, carbocyclic, or heterocyclic group, or may be bonded together to form a 5, 6 or 7 membered ring. By 5, 6 or 7 membered ring it is meant any of the carbocyclic rings previously described that comprise the requisite number of carbon atoms in their ring structure. $R^1$ and $R^2$ are preferably independently selected from hydrogen or an alkyl having from 1 to 8 carbon atoms.

More preferably, the couplers are represented by the formula:

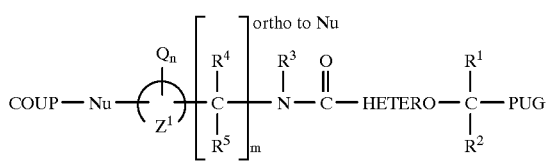

wherein COUP, Nu, HETERO, $R^1$, $R^2$ and PUG are as defined above. $Q_n$ in such a coupler is also as described above, with n being 0 to 3; that is, Q is independently selected from the group consisting of an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy, or arylthio group. $Z^1$ are the atoms necessary to complete a mono or bicyclic aromatic or heterocyclic ring system containing 5 to 10 ring atoms, such as those described previously for heterocyclic and carbocyclic groups in the definition of coupler substituents. $R^3$, $R^4$ and $R^5$ are independently selected from hydrogen, or an aliphatic, carbocyclic, or heterocyclic group, or two of $R^3$, $R^4$ and $R^5$ may be bonded together in a pair to form a 5, 6, or 7 membered ring. And m is selected from 0, 1, 2 or 3.

In the above structure, the term "ortho to Nu" refers to a favorable spatial relationship for nucleophilic attack of the nucleophilic group (Nu) on the electrophilic group (E).

Another preferred coupler is represented by the formula:

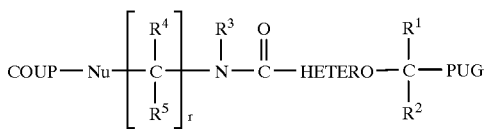

wherein COUP, Nu, HETERO, $R^1$, $R^2$ and PUG are as defined above, and $R^3$, $R^4$ and $R^5$ are independently selected from hydrogen, or an aliphatic, carbocyclic, or heterocyclic group, or two of $R^3$, $R^4$, or $R^5$ may be bonded together in a pair to form a 5, 6, or 7 membered ring. r is selected from 0, 1, 2, 3, 4 or 5, and is preferably 2, 3 or 4.

More preferred couplers utilized in the invention are represented by the formula:

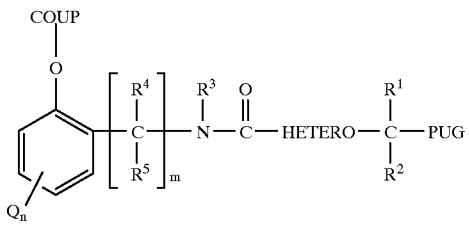

wherein COUP, Q, $R^1$ to $R^5$, m, n, HETERO, and PUG are as defined above.

The couplers utilized in the invention, as described above, contain a heterocyclic group (HETERO) separating $T^1$ from $C(R^1)(R^2)$-PUG. This group is preferably also a timing or linking group, although this is not required. A typical HETERO group is a heterocyclic group containing at least two heteroatoms independently selected from oxygen, sulfur or nitrogen. One of these heteroatoms is bonded directly to $T^1$; the other (or one of the others where there are more than two heteroatoms) can be bonded to the carbon which is bonded directly to PUG, but is typically not. Representative HETERO groups are described in European Patent Applications 0 499 279 and 0 438 129, both of which are incorporated herein by reference.

Specific heterocyclic groups suitable for the invention include pyrazoles, imidazoles, 1,2,3-triazoles, 1,2,4-triazoles, tetrazoles, indazoles, benzimidazoles, benzotriazoles, pyrazolotriazoles, pyrazoloimidazoles and triazoloimidazoles. Preferred are pyrazoles, imidazoles, 1,2,3-triazoles, 1,2,4-triazoles, tetrazoles, indazoles, benzimidazoles and benzotriazoles.

In a more preferred embodiment of the invention, HETERO is represented by the formula:

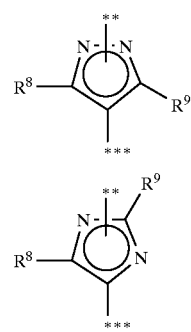

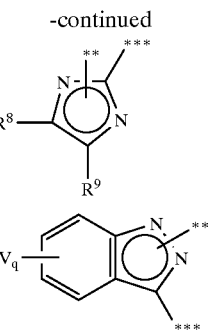

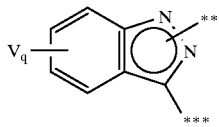

wherein
** designates the point of attachment of HETERO to T¹, wherein such attachment is through one of the nitrogen atoms in HETERO;
*** designates the point of attachment of HETERO to —C(R¹) (R²)-PUG;
$R^8$ and $R^9$ are independently selected from hydrogen or an aliphatic, carbocyclic or heterocyclic group, or a halo, carbamoyl, sulfomoyl, carbonamido, sulfonamido, nitro, hydroxyl, carboxyl, amino, or sulfo group, or may be bonded together to form a 5, 6 or 7 membered ring; and are preferably hydrogen, an alkyl of 1 to 8 carbon atoms, nitro, sulfonamido or a carbonamido group;

V is selected from an alkyl, heterocyclic, halo, carbamoyl, sulfamoyl, carbonamido, sulfonamido, keto, sulfo, nitro, hydroxyl, carboxyl, amino, alkoxy, alkoxycarbonyl, aryloxy or arylthio group; and is preferably an alkyl of 1 to 8 carbon atoms; and q is 0, 1, 2, 3, or 4.

The coupler utilized in the invention releases a PUG precursor upon coupling during processing. The PUG can be any PUG known in the art. Examples include development inhibitors, bleach accelerators, development accelerators, dyes, bleach inhibitors, couplers, developers, silver complexing agents, fixing agents, image toners, stabilizers, hardeners, tanning agents, fogging agents, ultraviolet radiation absorbers, antifoggants, nucleators, chemical or spectral sensitizers, and desensitizers. Other PUGs known in the art are also possible in the present invention. These PUGs, as well as those specifically described above, can be released from HETERO—C(R¹)(R²)— in the form of a precursor which, upon subsequent reaction, such as redox reaction with a component of the developing solution, releases the PUG.

PUG may also be representative of two or more of the above groups. In this regard, for example, it is contemplated that upon coupling and release of T¹ from COUP, HETERO could further release two development inhibitors, two bleach accelerators, or a combination of a bleach accelerator and development inhibitor.

Couplers which release development inhibitors can enhance the effects heretofore obtained with untimed or unlinked DIR couplers since they can release a development inhibitor at a distance from the point at which oxidized color developing agent reacted with the coupler, in which case they can provide, for example, enhanced interlayer interimage effects.

Couplers as described which release bleach inhibitors or bleach accelerators can be employed in the ways described in the photographic art to inhibit the bleaching of silver or accelerated bleaching in areas of a photographic element.

Couplers as described which release a dye or dye precursor can be used in processes where the dye is allowed to diffuse to an integral or separate receiving layer to form a desired image. Alternatively, the dye can be retained in the location where it is released to augment the density of the dye formed from the coupler from which it is released or to modify or correct the hue of that dye or another dye. In another embodiment, the dye can be completely removed from the element and the dye which was not released from the coupler can be retained in the element as a color correcting mask.

Couplers as described in which the PUG is a developing agent can be used to release a developing agent which will compete with the color forming developing agent, and thus reduce dye density.

In the preferred embodiment of the invention the PUG is a development inhibitor. More preferably it is selected from a mercaptotetrazole, mercaptotriazole, dimercaptothiadiazole, mercaptooxadiazoles, mercaptoimidazole, mercaptobenzoimidazole, mercaptobenzoxazole, mercaptobenzothiazole, mercaptothiadiazole, tetrazole, 1,2,3-triazole, 1,2,4-triazole or benzotriazole.

Representative PUGs suitable for use in the present invention can be found in the following references, all of which are incorporated herein by reference: U.S. Pat. Nos. 3,227,554; 3,384,657; 3,615,506; 3,617,291; 3,733.201 and U.K. Pat. No. 1,450,479 (development inhibitors); U.S. Pat. Nos. 3,880,658; 3,931,144; 3,932,380; 3,932,381; 3,942,987, and 4,840,884 (dye and dye precursors); "On the Chemistry of white Couplers," by W. Puschel, Agfa-Gevaert AG Mitteilungen and der Forschungs-Laboratorium der Agfa-Gevaert AG, Springer Verlag, 1954, pp. 352–367; U.S. Pat. Nos. 2,998,314; 2,808,329; 2,689,793; 2,742,832; German Pat. No. 1,168,769 and British Pat. No. 907,274 (couplers); U.S. Pat. Nos. 2,193,015; 2,108,243; 2,592,364; 3,656,950; 3,658,525; 2,751,297; 2,289,367; 2,772,282; 2,743,279; 2,753,256 and 2,304,953 (developing agents); U.S. Pat. Nos. 3,705,801; 3,715,208; and German OLS No. 2,405,279 (bleach inhibitors); U.S. Pat. Nos. 4,912,024; 5,063,145, columns 21–22, lines 1–70; and EP Patent No 0,193,389 (bleach accelerators); and U.S. Pat. Nos. 4,209,580; 4,463,081; 4,471,045; and 4,481,287 and in published Japanese patent application No. 62-123,172 (electron transfer agents).

Specific couplers suitable for use in the invention are as follows:

DIR coupler I-1
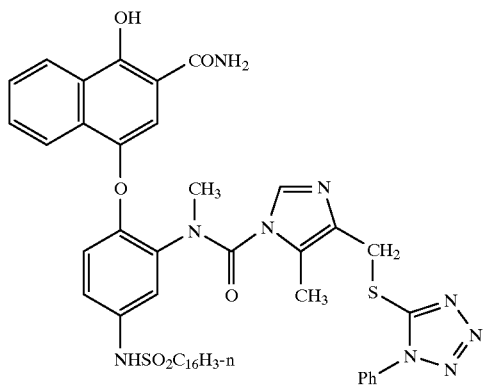
DIR coupler I-2
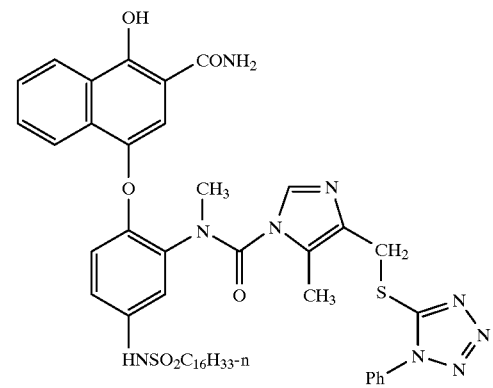
DIR coupler I-3
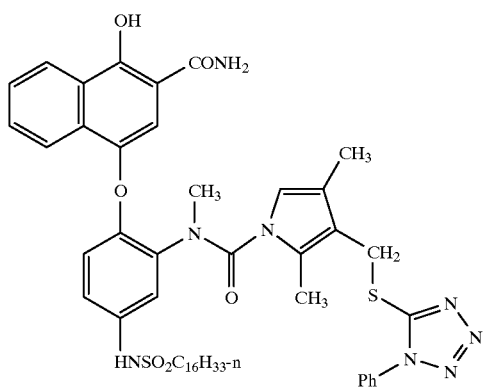
DIR coupler I-4
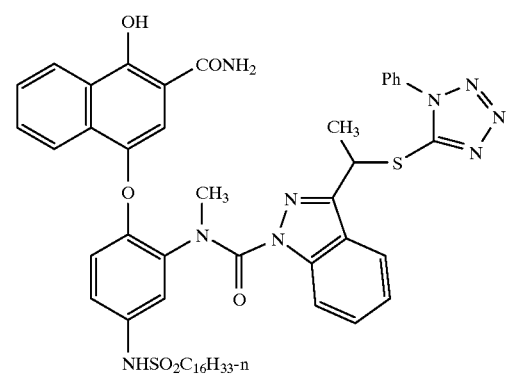
DIR coupler I-5
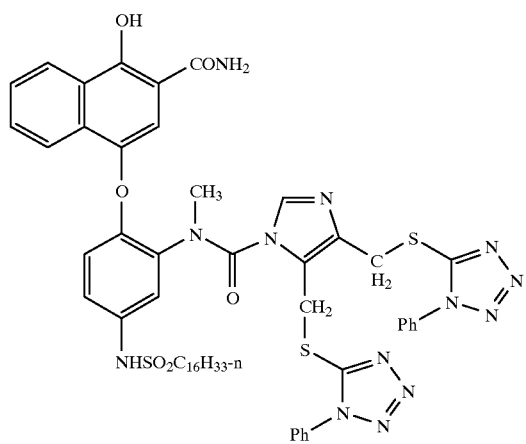
DIR coupler I-6
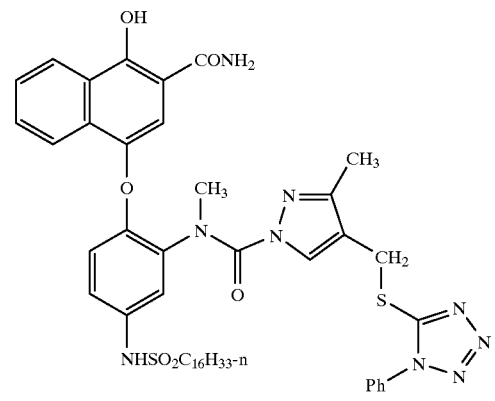

DIR coupler I-7
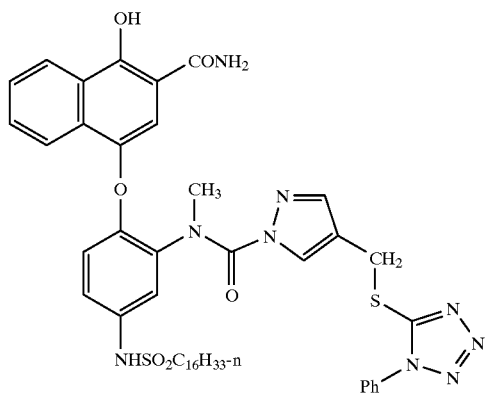
DIR coupler I-8
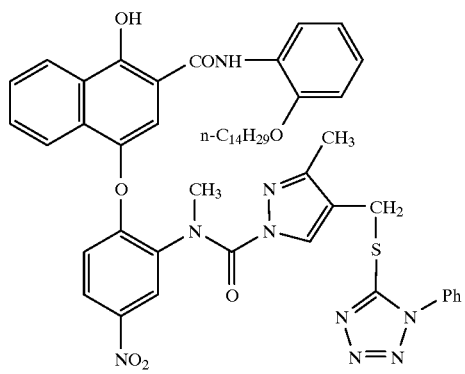
DIR coupler I-9
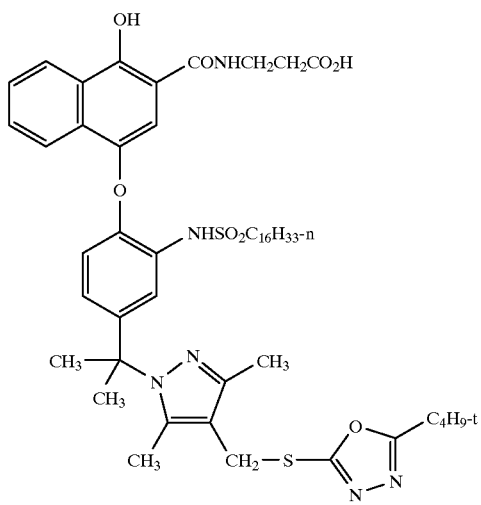
DIR coupler I-10
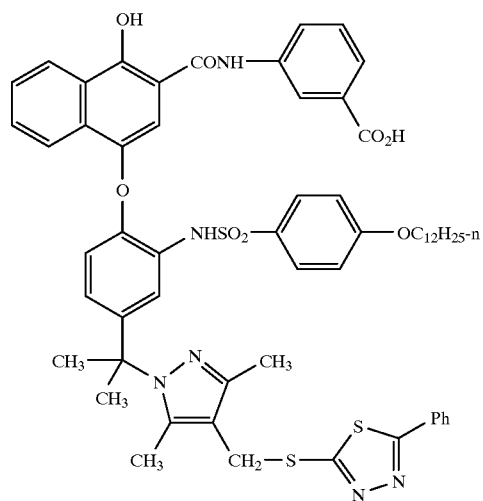
BAR coupler I-11
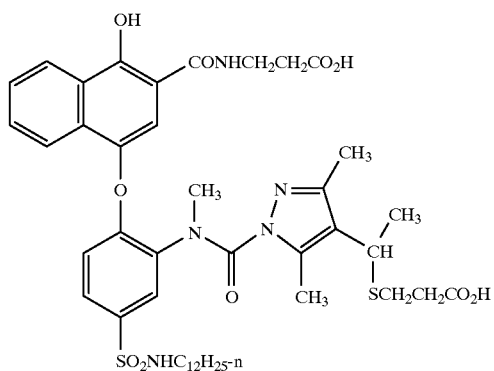
DIR coupler I-12
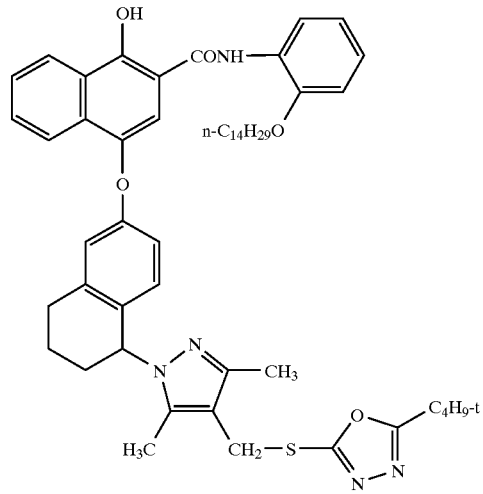

Coupler I-13
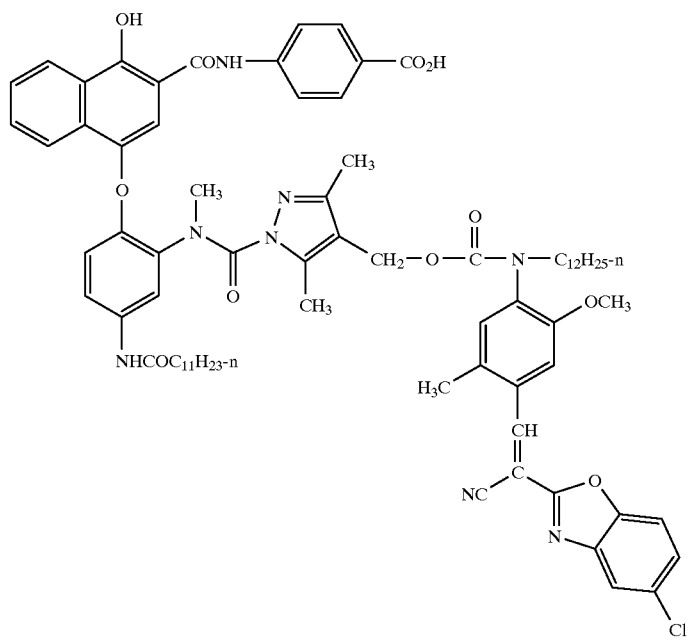
Coupler I-14
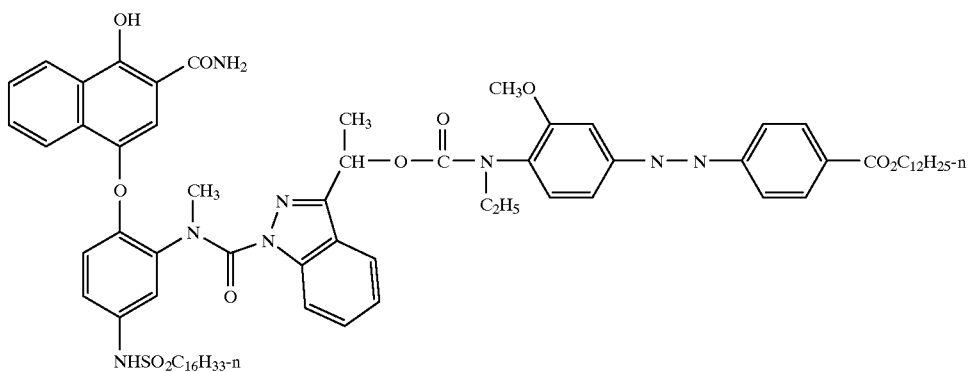
Coupler I-15
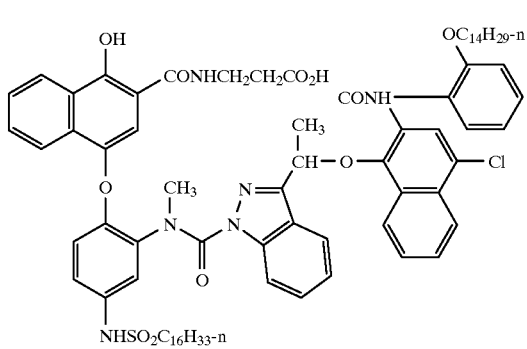
DIR coupler I-16
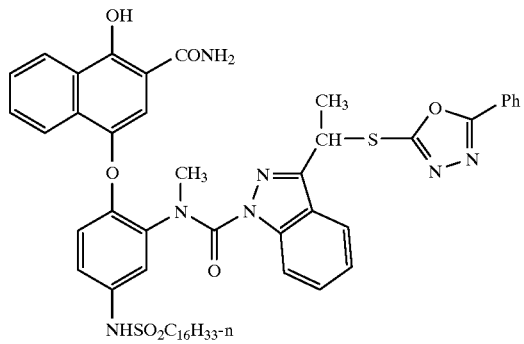

-continued

DIR coupler I-17

DIR coupler I-18

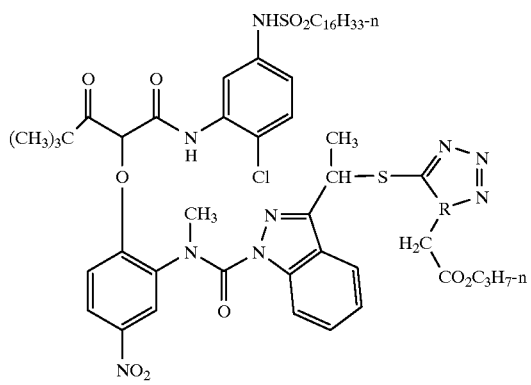

DIR coupler I-19

DIR coupler I-20

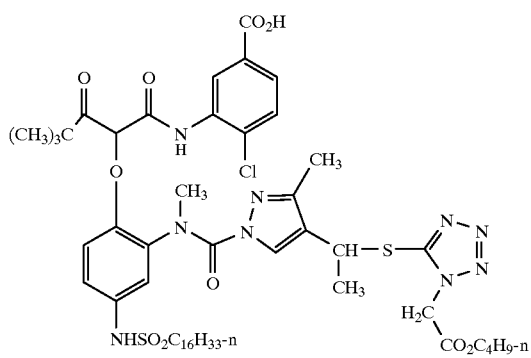

DIR coupler I-21

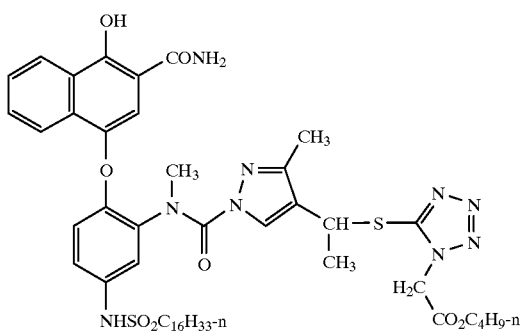

The photographic couplers can be incorporated in photographic elements by means and processes known in the photographic art. Photographic elements in which the couplers are incorporated can be simple elements comprising a support and a single silver halide emulsion layer or multilayer, multicolor elements. The couplers can be incorporated in at least one of the silver halide emulsion layers and/or in at least one other layer, such as an adjacent layer, where they will come into reactive association with oxidized color developing agent which has developed silver halide in the emulsion layer.

The silver halide emulsion layer can contain or have associated with it other photographic couplers such as dye-forming couplers, colored masking couplers, and/or competing couplers. These other photographic couplers can form dyes of any color and hue. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye imageproviding material, a green-sensitive silver halide emulsion unit having associated therewith a magenta dye image-providing material and a blue-sensitive silver halide emulsion unit having associated therewith a yellow dye image-providing material, at least one of the silver halide emulsion units or another layer having associated therewith a photographic coupler as described above. Each silver halide emulsion unit can be composed of one or more layers and the various units and layers can be arranged in different locations with respect to one another.

The light sensitive silver halide emulsions can include coarse, regular or fine grain silver halide crystals or mixtures thereof, in a hydrophobic colloid, such as gelatin. The crystals can be comprised of silver chloride, silver bromide, silver bromoiodide, silver chlorobromide, silver chloroiodide, silver chlorobromoiodide and mixtures thereof. The emulsions can be negative-working or positive-working emulsions and can be incorporated into negative or reversal elements, as well as other types of elements known in the art. They can form latent images predominantly on the surface of the silver halide grains or predominantly on the interior of the silver halide grains. They can be chemically and spectrally sensitized by methods known in the art.

The photographic element may contain a transparent magnetic recording layer such as a layer containing magnetic particles on the underside of a transparent support, as in U.S. Pat. Nos. 4,279,945 and 4,302,523 and *Research Disclosure*, November 1993, Item 3490, which are incorporated herein by reference. Typically, the element will have a total thickness (excluding the support) of from about 5 to about 30 microns.

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as with electron beam, beta radiation, gamma radiation, x-ray, alpha particle, neutron radiation, and other forms of corpuscular and wave-like radiant energy in either noncoherent (random phase) forms or coherent (in phase) forms, as produced by lasers. When the photographic elements are intended to be exposed by x-rays, they can include features found in conventional radiographic elements.

The photographic elements are preferably exposed to actinic radiation, typically in the visible region of the spectrum, to form a latent image, and then processed to form a visible dye image. Development is typically followed by the conventional steps of bleaching, fixing, or bleach-fixing, to remove silver or silver halide, washing, and drying.

In the following Table, reference will be made to (1) *Research Disclosure*, December 1978, Item 17643, (2) *Research Disclosure*, December 1989, Item 308119, (3) *Research Disclosure*, September 1994, Item 36544, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the photographic element according to the invention.

The Table and its cited references also describe suitable ways of exposing, processing and manipulating the elements, and the images contained therein.

| Reference | Section | Subject Matter |
|---|---|---|
| 1 | I, II | Grain composition, morphology |
| 2 | I, II, IX, X, XI, XII, XIV, | and preparation; Emulsion preparation including hardeners, coating aids, addenda, etc. |
| 3 | XV I, II, III, IV, A & B | |
| 1 | III, IV | Chemical sensitization and spectral sensitization/ desensitization |
| 2 | III, IV | |
| 3 | IV, V | |
| 1 | V | UV dyes, optical brighteners, luminescent dyes |
| 2 | V | |
| 3 | VI | |
| 1 | VI | Antifoggants and stabilizers |
| 2 | VI | |
| 3 | VII | |
| 1 | VIII | Absorbing and scattering materials; Antistatic layers; matting agents |
| 2 | VIII, XIII, XVI | |
| 3 | VIII, IX C & D | |
| 1 | VII | Image-couplers and image-modifying couplers; Dye stabilizers and hue modifiers |
| 2 | VII | |
| 3 | X | |
| 1 | XVII | Supports |
| 2 | XVII | |
| 3 | XV | |
| 3 | XI | Specific layer arrangements |
| 3 | XII, XIII | Negative working emulsions; Direct positive emulsions |
| 2 | XVIII | Exposure |
| 3 | XVI | |
| 1 | XIX, XX | Chemical processing; Developing agents |
| 2 | XIX, XX, XXII | |
| 3 | XVIII, XIX, XX | |
| 3 | XIV | Scanning and digital processing procedures |

SYNTHETIC EXAMPLE

The following synthetic example illustrates the synthesis of a coupler suitable for use in the invention. It is intended to be illustrative, and can be readily modified by one of ordinary skill in the art to obtain other suitable couplers.

Synthesis of DIR Coupler I-3

Intermediate A-1

Ethyl diacetoacetate (68.8 g, 0.4 Mole) was dissolved in 20% aqueous acetic acid (400 mL). This solution was cooled to 10° C. and with stirring, hydrazine hydrate (20 mL, 0.4 Mole) was added dropwise keeping the temperature at 15–20° C. At the end of the addition, the solution was stirred at room temperature for 12 hours. The solution was then concentrated under reduced pressure, and co-evaporated with heptane several times. The residue was dissolved in heptane a final time whereupon the product A-1, crystallized out.

Intermediate A-2

Lithium aluminium hydride (3.2 g, 84.44 mMole), was suspended in dry tertahydrofuran (100 mL) and stirred at 0° C. Intermediate A-1 (10.0 g, 73.42 mMole) was added slowly while maintaining the temperature at 0° C. After all of intermediate A-1 had been added, the solution was allowed to warm to room temperature and the resulting mixture was stirred for 12 hours. The reaction was then cooled to 0° C. again and carefully quenched with water (5 mL). The mixture was then concentrated under reduced pressure, treated with methanol (200 mL) and heated to reflux while passing through it a stream of carbon dioxide. After 30 minutes the mixture was filtered over celite and the residue was washed with boiling methanol. The methanol washings and the filtrate were combined and concentrated under reduced pressure to yield A-2 as an oil.

Intermediate A-3

The preparation of this intermediate is found in U.S. Pat. Nos. 5,264,582 and 5,288,593, incorporated herein by reference.

Intermediate A-4

Intermediate A-3 (7.4 mMole), was dissolved in dry pyridine (30 mL) and intermediate A-2 (1.11 g, 8.8 mMole) added. The resulting solution was stirred at room temperature for 12 hours. The reaction solution was then diluted with ethyl acetate and washed with 2N–HCl (x2). The organic layer was collected, dried over $MgSO_4$, filtered and concentrated to an oil under reduced pressure. This oil was dissolved in 45% ethyl acetate in heptane and subjected to medium pressure chromatography over silica gel eluting with 45% ethyl acetate in heptane. The first major component was collected and concentrated to an oil, yielding Intermediate A-4.

Intermediate A-5

Intermediate A-4 (3.2 g, 4.2 mMole), was dissolved in ethyl acetate (30 mL) and treated with thionyl chloride (8.4 mMole, 0.61 mL) with stirring. The resulting yellow solution was stirred at room temperature for 30 minutes and then concentrated under reduced pressure. The residue was dissolved in ethyl acetate and concentrated again. This procedure was repeated several times to remove any excess sulphuryl chloride.

DIR Coupler I-3

Intermediate A-4 (4.2 mMoles) was dissolved in dimethylforamide (30 mL) and the sodium salt of phenyl mercaptotetrazole, NaPMT, (0.84 g, 4.2 mMole) was added. The resulting solution was stirred at room temperature for 30 minutes and then diluted with ethyl acetate. The ethyl acetate solution was washed with 2N—HCl (x2), dried over $MgSO_4$, filtered and concentrated to an oil under reduced pressure. This oil was dissolved in 40% ethyl acetate in heptane and subjected to medium pressure chromatography over silica gel eluting with 40% ethyl acetate in heptane. The first major component was collected and concentrated under reduced pressure to yield DIR Coupler I-3.

The above synthesis can be represented by the following scheme:

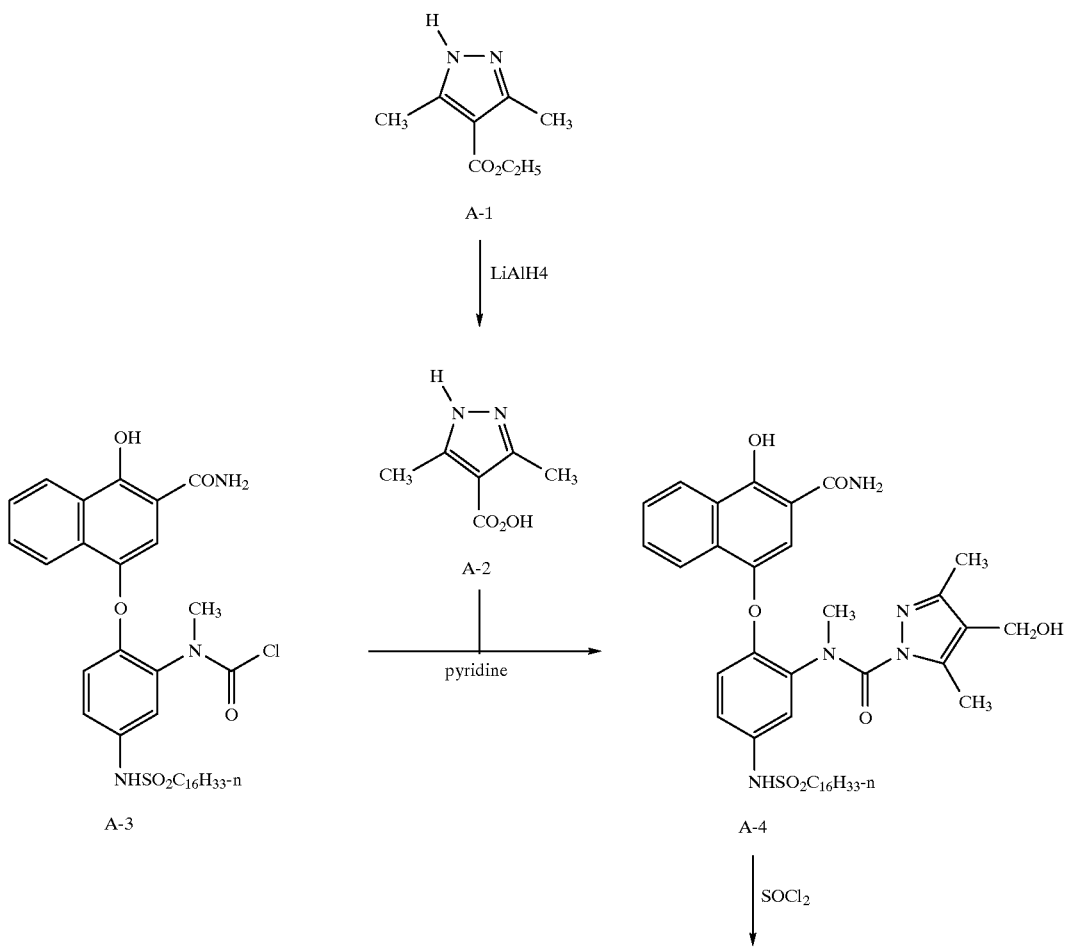

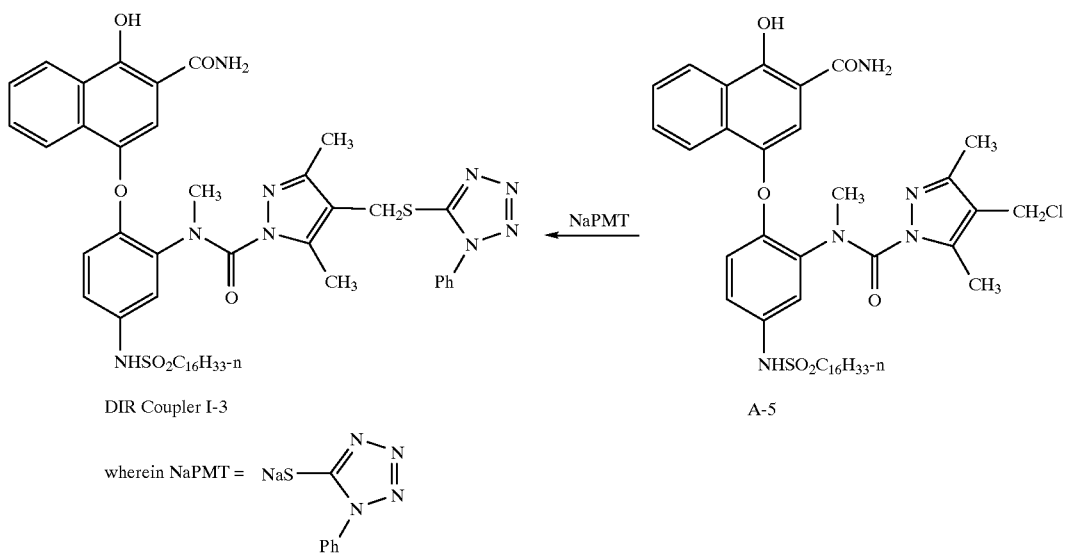

The following examples illustrate the practice of the invention. They are intended to be illustrative, and should not be construed as limiting the invention to the specific embodiments disclosed.

EXAMPLES

Photographic elements were prepared by coating the following layers on a cellulose ester film support (amounts of each component are indicated in mg/m$^2$)

| | |
|---|---|
| Emulsion layer 1: | Gelatin-2420; red sensitized silver bromoiodide (as Ag)-1615; yellow image coupler (Y-1), dispersed in dibutyl phthalate. (RECEIVER LAYER) |
| Interlayer: | Gelatin-860; didodecylhydroquinone-113 |
| Emulsion layer 2: | Gelatin-2690; green sensitized silver bromoiodide (as Ag)-1615; magenta image coupler (M-1), dispersed in tritolyl phosphate; DIR coupler of Tables 1 or 2 dispersed in N,N-diethyl-dodecanamide. (CAUSER LAYER) |
| Protective Overcoat | Gelatin-5380; bisvinylsulfonylmethyl ether at 2% total gelatin. |

Structures of couplers utilized in the Examples and not previously described are as follows:

Magenta Image Coupler, M-1:
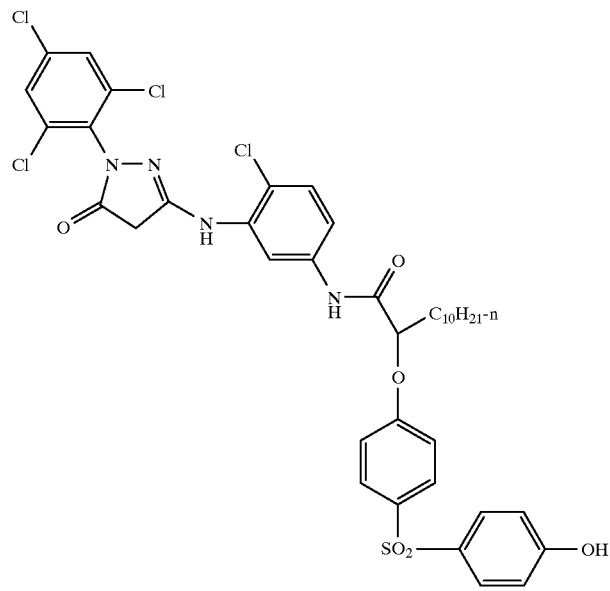
Yellow Image Coupler, Y-1:
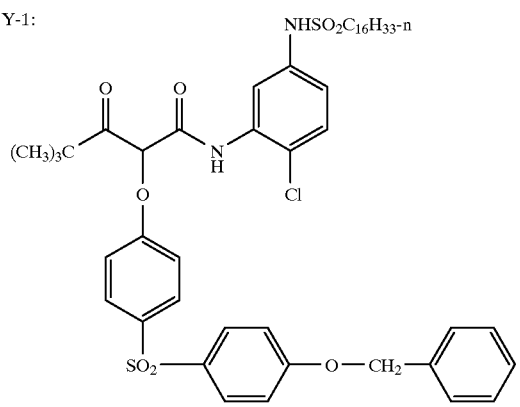
DIR Coupler: C-1
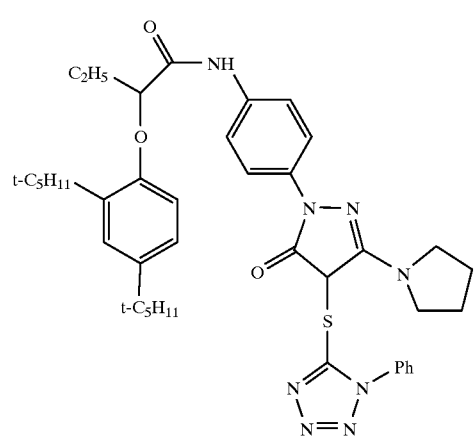

DIR Coupler: C-2

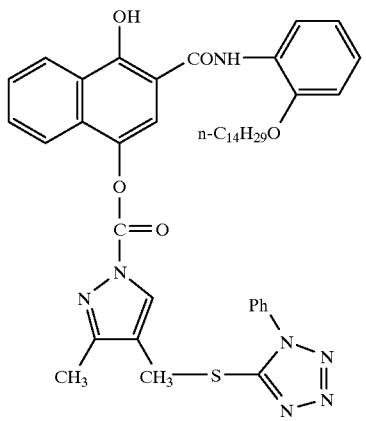

Strips of each element were exposed to green light through a graduated density step tablet, or through a 35% modulation fringe chart for sharpness measurements, and then developed for 3.25 minutes at 38° C. in the following color developer. Development was then stopped, and the elements washed, bleached, fixed, washed and dried.

| Color Developer | |
|---|---|
| Distilled water | 800 mL |
| Sodium Metabisulfite | 2.78 g |
| Sodium Sulfite, anhydrous | 0.38 g |
| CD-4 ™ (color developer)* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate | 2.41 g |
| Diethylenetriaminepentacetic acid, pentasodium salt (40% Soln.) | 8.43 g |
| Distilled water | to 1 L |
| Adjust pH to 10.0. | |

*CD-4 ™ is a KODAK color developer in which the active component is 4-amino-3-methyl-N-ethyl-N-beta-hydroxy-ethylaniline sulfate.

Stability of the couplers utilized in the invention and the comparative couplers is shown in Table I as % loss. Specifically, % loss was determined by extracting the coupler from elements incubated in high temperature and high humidity conditions, and comparing the amount (weight) of coupler extracted with the amount (weight) extracted from similar elements that were not incubated. Extraction was performed by methods known in the art and measurements of coupler amounts were made by HPLC analysis.

Photographic effects were determined as follows: To determine acutance(AMT), a series of elements as described above containing no DIR coupler or varying levels of DIR coupler were exposed with green light. The contrast ($\gamma$) along the straight line portion of each elements' D log H curve was measured. A plot of log($\gamma$) versus amount of DIR coupler ($\mu$mnoles) was made for each element (each element containing a different DIR coupler). From these plots, the amount of DIR coupler needed to achieve log($\gamma_o/2$) was read, where $\gamma_o$ represented the contrast of the element containing no DIR coupler. This value was recorded in the Tables 1 and 2 as Amount* (* amount of DIR coupler need to reduce the contrast by 50%). In the same experiment, a plot of acutance versus log($\gamma$) was made for each element and from this plot the acutance at position log($\gamma_o/2$) was read. These acutance values are shown in Table 2.

Acutance, as measured by AMT values and recorded in Table 2, are calculated using the following formula in which the cascaded area under the system modulation curve is shown in equation (21.104) on page 629 of the "Theory of the Photographic Process", 4th Edition, 1977, edited by T. H. James: AMT 100+66Log[cascaded area/2.6696 M] wherein the magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009–12, (1973). AMT is a further modification of CMT useful for evaluating systems which include the viewing of a positive print made from a negative.

Interlayer interimage effects representing the degree of color correction capable of being obtained by practice of the invention were evaluated after the same series of photographic elements were exposed to white light. The log of the causer contrast($\gamma_c$) and the log of the receiver contrast ($\gamma_r$) were read for each of the DIR levels in the elements and a plot of log($\gamma_c$) versus log($\gamma_r$) was made. From this plot, ($\gamma_r$) was determined at log($\gamma_o/2$), where log ($\gamma_o/2$) was measured along the causer axis in the plot. The ratio ($\gamma_c$)/($\gamma_r$) was recorded in Table 2 as Interlayer Interimage.

TABLE 1

| Coupler | Amount* $\mu$moles/m$^2$ | % Loss** |
|---|---|---|
| C-1 | 134.1 | 2.5 |
| C-2 | 96.8 | 5 |
| I-1 | 139.9 | 2 |
| I-2 | 143.1 | 0 |
| I-3 | 120.5 | 0 |
| I-4 | 129.1 | 0 |
| I-7 | 322.8 | 0 |
| I-8 | 129.1 | 0 |

*Amount of the DIR coupler coated that is needed to reduce contrast 50%.
**% loss of the coupler from the photographic elements after 2 weeks at 49° C. and 50% relative humidity.

TABLE 2

| Coupler | Amount* $\mu$moles/m$^2$ | Interlayer Interimage ($\gamma c/\gamma r$) | Accutance (35 mm/causer) |
|---|---|---|---|
| C-1 | 134.1 | 2.32 | 91.0 |
| C-2 | 96.8 | 3.10 | 94.8 |

TABLE 2-continued

| Coupler | Amount* $\mu$moles/m$^2$ | Interlayer Interimage ($\gamma$c/$\gamma$r) | Accutance (35 mm/causer) |
|---|---|---|---|
| I-1 | 139.9 | 2.44 | 91.6 |
| I-2 | 143.1 | 2.63 | 93.6 |
| I-3 | 120.5 | 2.63 | 91.7 |
| I-4 | 129.1 | 2.38 | 90.7 |
| I-5 | 252.8 | 2.38 | 91.4 |
| I-6 | 158.2 | 3.39 | 93.8 |
| I-7 | 322.8 | 3.56 | 93.6 |

*Amount of the DIR coupler coated that is needed to reduce contrast 50%.

It can be seen from Tables 1 and 2 that the couplers utilized in this invention have superior stability when stored under tropical conditions. Furthermore, when releasing a development inhibitor, they provide for improved sharpness and interlayer interimage.

The invention has been described in detail with particular reference to preferred embodiments thereof, but it will be understood that variations and modifications can be effected within the spirit and scope of the invention.

What is claimed is:

1. A photographic coupler represented by the formula

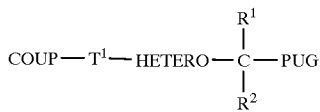

wherein
COUP is a coupler moiety having a coupling site to which $T^1$ is attached;
$T^1$ is a timing or linking group which releases from COUP during processing and which functions by electron transfer down a conjugated chain, or by nucleophilic displacement reaction, to release from HETERO;
HETERO is a heterocyclic group containing at least two heteroatoms independently selected from oxygen, nitrogen, or sulfur, wherein one of the heteroatoms is directly attached to $T^1$;
$R^1$ and $R^2$ are independently selected from hydrogen, or an aliphatic, carbocyclic, or heterocyclic group, or may be bonded together to form a 5, 6, or 7 membered ring; and
PUG is a photographically useful group.

2. A photographic coupler in accordance with claim 1 wherein the coupler is represented by the formula

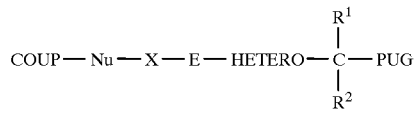

wherein
COUP, HETERO, $R^1$, $R^2$, and PUG are as defined in claim 1;
Nu is a nucleophilic group which is attached to the coupling site of COUP and which is displaced therefrom upon reaction of COUP with oxidized color developing agent during processing;
E is an electrophilic group which is attached to HETERO and which is displaced therefrom by Nu after Nu is displaced from COUP; and
X is a linking group for spatially relating Nu and E so that upon displacement of Nu from COUP, Nu-X-E undergoes a nucleophilic displacement reaction with the formation of a three to eight membered ring and the cleavage of the bond between E and HETERO.

* * * * *